United States Patent [19]

Quarderer, Jr. et al.

[11] Patent Number: 5,486,627

[45] Date of Patent: Jan. 23, 1996

[54] METHOD FOR PRODUCING EPOXIDES

[75] Inventors: George J. Quarderer, Jr., Midland, Mich.; Curtis N. Swisher; David L. Trent, both of Lake Jackson, Tex.

[73] Assignee: The Dow Chemical Company, Midland, Mich.

[21] Appl. No.: 348,639

[22] Filed: Dec. 2, 1994

[51] Int. Cl.$^6$ .................. C07D 301/26; C07D 303/04; C07D 303/08; C07D 303/14

[52] U.S. Cl. .............. 549/521; 549/520; 549/522; 568/812; 568/832; 568/847; 568/848; 568/850

[58] Field of Search .................. 549/520, 521, 549/522

[56] References Cited

U.S. PATENT DOCUMENTS

| | | | |
|---|---|---|---|
| 1,308,796 | 7/1919 | McElroy . | |
| 1,510,790 | 3/1924 | McElroy . | |
| 1,996,638 | 4/1935 | Britton et al. | 260/156.5 |
| 2,155,281 | 4/1939 | Muskat et al. | 23/152 |
| 2,157,524 | 5/1939 | Cady | 23/152 |
| 2,157,525 | 5/1939 | Cady | 23/152 |
| 2,188,254 | 1/1940 | Smithuysen | 202/42 |
| 2,240,344 | 4/1941 | Muskat et al. | 23/152 |
| 2,347,151 | 4/1944 | Crawford et al. | 23/152 |
| 3,282,966 | 11/1966 | Naugle, Jr. et al. | 260/348.6 |
| 3,398,062 | 8/1968 | Tsao et al. | 203/78 |
| 3,455,797 | 7/1969 | Courtier | 204/80 |
| 3,457,282 | 7/1969 | Polak et al. | 549/521 |
| 3,578,400 | 5/1971 | Wojtowicz et al. | 23/152 |
| 3,718,598 | 2/1973 | Wojtowicz et al. | 252/187 |
| 3,845,145 | 10/1974 | Wojtowicz et al. | 568/850 |
| 3,886,187 | 5/1975 | Bartholomé et al. | 260/348.6 |
| 3,894,059 | 7/1975 | Silvarstrom | 549/522 |
| 3,914,397 | 10/1975 | Mueller | 423/427 |
| 4,008,133 | 2/1977 | Gelbein et al. | 204/80 |
| 4,126,526 | 11/1978 | Kwon et al. | 549/522 |
| 4,146,578 | 3/1979 | Brennan et al. | 423/473 |
| 4,147,761 | 4/1979 | Wojtowicz et al. | 423/473 |
| 4,190,638 | 2/1980 | Hoekje et al. | 423/473 |
| 4,240,885 | 12/1980 | Suciu et al. | 204/98 |
| 4,243,492 | 1/1981 | Yamamura et al. | 203/8 |
| 4,277,405 | 7/1981 | Apanel | 260/348.21 |
| 4,415,460 | 11/1983 | Suciu et al. | 210/754 |
| 4,496,753 | 1/1985 | Kwon et al. | 549/521 |
| 4,504,456 | 3/1985 | Yant et al. | 423/473 |
| 4,584,178 | 4/1986 | Yant et al. | 422/140 |
| 4,744,956 | 5/1988 | Yant et al. | 422/106 |
| 5,146,011 | 9/1992 | Shen et al. | 568/844 |

FOREIGN PATENT DOCUMENTS

| | | |
|---|---|---|
| 952285 | 8/1974 | Canada . |
| 543944 | 9/1940 | United Kingdom . |
| 1358839 | 8/1970 | United Kingdom . |

OTHER PUBLICATIONS

K. H. Simmrock, "Compare propylene oxide routes", *Hydrocarbon Processing*, Nov. 1978 pp. 105–113.

Bikbulatov, "Chlorohydrins", Siberian Chemistry Journal, 1984, pp. 124–127 (Translation).

Bikbulatov et al., "A New Scheme of Synthesis of Glycerol Dichlorohydrins", The Soviet Chemical Industry, 1985, pp. 658–660.

Bikbulaov, et al., "Nonaqueous Solution of Hypochlorous Acid and Chlorohydrination Reactions of Certain Lower Alkenes", Zjurnal Prikladnoi Khimii, vol. 58, No. 11 pp. 2499–2503 (Translation) (1985).

Bikbulatov et al., "A New Scheme for Production of Hypochlorous Acid in Production of Epichlorohydrin", The Soviet chemical industry, 1984, pp. 418–420.

*Primary Examiner*—Joseph E. Evans
*Attorney, Agent, or Firm*—John B. Treangen

[57] ABSTRACT

Described herein is a method for producing epoxides which is continuous, inhibits formation of chlorinated byproducts, and eliminates or substantially reduces waste water discharge. The method includes:

(a) forming a low chlorides aqueous hypochlorous acid solution;

(b) contacting the low chlorides aqueous hypochlorous acid solution with at least one unsaturated organic compound to form an aqueous organic product comprising at least olefin chlorohydrin;

(c) contacting at least the olefin chlorohydrin with an aqueous alkali metal hydroxide to form an aqueous salt solution product containing at least epoxide; and (d) isolating the epoxide from the aqueous salt solution; wherein water is recovered from the product of at least Step (b) and recycled into Step (a) for use in forming the low chlorides aqueous hypochlorous acid solution. In this process, not only is the water internally recycled after Step (b), but a concentrated brine solution is generated in both Steps (a) and (d) which is useful in other processes such as electrochemical production of chlorine and caustic. The chlorine and caustic, in turn, may then be recycled back to the method of this invention.

32 Claims, No Drawings

METHOD FOR PRODUCING EPOXIDES

BACKGROUND AND SUMMARY OF THE INVENTION

The present invention relates to production of olefin oxides (epoxides), particularly to processes for forming the epoxides via the corresponding halohydrin processes.

Halohydrin processes for the production of epoxides, including ethylene oxide, propylene oxide, butylene oxide, epichlorohydrin, and the like, advantageously involve the reaction of chlorine (or other halogen or hypohalite) with the corresponding piefin (ethylene, propylene, butene, allyl chloride, respectively) in aqueous solution to produce an intermediate halohydrin. The halohydrin may then be reacted with a base to produce the desired epoxide and brine. The epoxide is advantageously stripped from the brine and is optionally separated from various byproducts. The brine is optionally treated for removal of residual impurities. There are numerous variations on each of these reactions.

A particularly advantageous variation of the halohydrin process is the use of low-chlorides aqueous hypochlorous acid (HOCl), in place of chlorine gas, for reacting with the piefin. This HOCl variation is advantageous because of a resulting increased selectivity for the desired epoxides. Chloride ions are preferably in low concentrations because they contribute to the production of undesirable chlorinated organic byproducts such as di- and trichlorides and they accelerate decomposition of HOCl to chlorates. A problem with the halohydrin process, however, is that there is a significant amount of waste water discharge from the process. For example, in the production of one kilogram (kg) of propylene oxide product, typically greater than 40 kg of water containing various undesirable organic byproducts and about 5–10 weight percent (wt-%) sodium chloride salt or 5–6 wt-% calcium chloride salt is generated. These aqueous waste streams are of little or no commercial value and therefore must be discharged after suitable treatment. See K. H. Simmrock, "Compare Propylene Oxide Routes", 57 *Hydrocarbon Processing* 109–10 (November 1978).

Therefore, there is a need for a low chlorides HOCl process for producing epoxides that substantially reduces or eliminates waste water discharge. The present invention is a method for producing epoxides comprising the steps:

(a) forming a low chlorides aqueous hypochlorous acid solution;

(b) contacting the low chlorides aqueous hypochlorous acid solution with at least one unsaturated organic compound to form an aqueous organic product comprising at least olefin chlorohydrin, wherein the unsaturated organic compound contains from 2 to about 10 carbon atoms and is selected from the group consisting of substituted and unsubstituted olefins and cyclic olefins, the substituted olefins having substituents selected from the group consisting of an alkyl radical, a phenyl radical, and an alkylphenyl radical, each radical being independently either unsubstituted or substituted;

(c) contacting at least the olefin chlorohydrin with an aqueous alkali metal hydroxide to form an aqueous salt solution product containing at least epoxide; and (d) isolating the epoxide from the aqueous salt solution; wherein water is recovered from the product of at least Step (b) and recycled into Step (a) for use in forming the low chlorides aqueous hypochlorous acid solution. Optionally, water in the form of a concentrated sodium chloride brine from Step (a) and Step (d) may be used as feed to an electrochemical cell for production of chlorine and caustic which, in turn, may be use in the method of this invention.

This method may be run continuously, inhibits formation of chlorinated byproducts, and substantially reduces or eliminates waste water discharge by, first, recycling water internally after Step (b) and, second, generating a concentrated brine solution in Step (a) and Step (d) that is useful in other processes such as electrochemical production of chlorine and caustic.

DETAILED DESCRIPTION OF THE INVENTION

The process of this invention requires a first step of forming a low chlorides aqueous HOCl solution. The term "low chlorides aqueous HOCl solution" is used to refer to a solution of hypochlorous acid in water having a hypochlorous acid concentration of at least about 1 weight percent, preferably at least about 3 weight percent, but less than about 10 weight percent, preferably less than about 7 weight percent, and which is substantially free of chloride ion. "Substantially free of chloride ion" is meant to mean preferably less than about 1000 parts per million (ppm) chloride ions in the aqueous HOCl solution, more preferably less than about 500 ppm chlorides, and most preferably less than about 200 ppm chlorides.

Many methods are known for forming low chlorides aqueous HOCl solutions and a few of these methods are discussed herein. One method is described in copending U.S. patent application Ser. No. 08/156,494 filed Nov. 23, 1993, now abandoned, and generally comprises the following steps:

(a) contacting an aqueous alkali metal hydroxide solution with chlorine to produce an aqueous alkali metal hypochlorite solution;

(b) contacting droplets of the aqueous alkali metal hypochlorite solution with chlorine gas to produce aqueous hypochlorous acid;

(c) vaporizing at least about 30 weight percent of the aqueous hypochlorous acid to produce a vapor phase and a liquid phase, the vapor phase comprising chlorine, water vapor, hypochlorous acid, and dichlorine monoxide, the liquid phase comprising hypochlorous acid in an aqueous salt solution;

(d) distilling the liquid phase using a vapor stripping stream containing at least about 20 mole percent chlorine to strip vapor phase hypochlorous acid and dichlorine monoxide from the aqueous salt solution; and (e) absorbing the vapor phase hypochlorous acid and dichlorine monoxide from both Steps (c) and (d) into water.

The specifics of this method are adequately disclosed in the aforementioned copending patent application and its teachings are incorporated herein by reference. After an initial run-through of the method for producing epoxides of this invention, the water of Step (e) in this HOCl method (Step (a) of the epoxide method), is comprised of water recycled from Step (b) of the epoxide method (discussed infra). Additional, non-recycled, water may also be supplemented to this recycled water. A preferred embodiment of this method for producing low chlorides aqueous HOCl solution comprises collecting gases after Step (e) and recycling the gases to Step (d). Typically, these gases comprise chlorine and chlorine containing compounds.

Preferably, the alkali metal hydroxide is either sodium or potassium hydroxide. More preferably, the alkali metal hydroxide is sodium hydroxide and the alkali metal hypochlorite is sodium hypochlorite. Most preferably, the sodium hydroxide is supplied as caustic from a chlor-alkali electrochemical cell. The chloralkali electrochemical cell, such as a diaphragm or membrane type cell, may be used as a recycling means for various waste aqueous salt solution streams ("brine") from the epoxide producing method of this invention. For example, a preferred aspect of this invention is to recycle the brine from the HOCl forming step (e.g. Step (d) of the HOCl method described above), to a chlor-alkali electrochemical cell. The chlor-alkali electrochemical cell then forms products such as chlorine gas and aqueous sodium hydroxide ("caustic") which may be used again in the method for producing epoxides. Similar methods for recycling brine streams are disclosed in U.S. Pat. Nos. 3,455,797 and 4,008,133 which are incorporated herein by reference.

Another method for forming the low chlorides aqueous HOCl solution comprises:

(a) contacting an aqueous alkali metal hydroxide solution with chlorine to produce an aqueous alkali metal hypochlorite solution;

(b) contacting droplets of the aqueous alkali metal hypochlorite solution with chlorine gas to produce hypochlorous acid in an aqueous salt solution;

(c) extracting the hypochlorous acid from the aqueous salt solution using an organic solvent;

(d) stripping the hypochlorous acid from the organic solvent using a non-reactive gas; and (e) absorbing the stripped hypochlorous acid into water.

As relates to Steps (a), (b), and (e), this method is the same as the HOCl method described previously. As in the first method, the alkali metal hydroxide is preferably sodium hydroxide and the alkali metal hypochlorite is preferably sodium hypochlorite. More preferably, the sodium hydroxide is supplied as caustic from the chlor-alkali electrochemical cell. However, in contrast to the previous HOCl method, an organic solvent is used to extract the HOCl from the aqueous salt solution in Step (c). Ketones, such as methyl isobutylketone, have been found to be particularly useful in this function. Specifics of a method utilizing organic solvents to extract HOCl are described in U.S. Pat. No. 3,578,400 (incorporated herein by reference).

After performing the extraction of the HOCl in Step (c), this method preferably further comprises distilling the raffinate aqueous salt solution using a vapor stripping stream to further strip hypochlorous acid and organic solvent from the solution. Prior to performing Step (d), the stripped HOCl and organic solvent may then be combined with the HOCl and organic solvent obtained from performing the extraction. Preferably, the aqueous salt solution remaining after performing the extraction of Step (c) is recycled to the chlor-alkali electrochemical cell, described previously, to form chlorine and caustic. The chlorine and caustic may then be recycled back for use in forming the low chlorides aqueous HOCl solution. It is generally preferred, prior to recycling into the chlor-alkali electrochemical cell, to remove any impurities from the brine. These impurities typically comprise traces of the organic solvent as well as HOCl decomposition products such as chloric acid and sodium chlorate. A method for removing these impurities may include acidification and chlorinolysis or absorption on carbon or zeolites as is well known in the art. Methods for removing impurities from brine before passing through a chloralkali electrochemical cell are described in copending U.S. application Ser. No. 08/156,507, filed Nov. 23, 1993, now abandoned, and U.S. Pat. Nos. 4,126,526, 4,240,885, and 4,415,460 each of which are incorporated herein by reference.

As stated in Step (d), the HOCl is stripped from the organic solvent using a non-reactive gas. Typically, this non-reactive gas is either nitrogen, water vapor, or a mixture of both. After stripping the HOCl in Step (d), the organic solvent may be recycled back to Step (c) for use in extracting the HOCl from the aqueous salt solution. Generally, the recycling should comprise, first, removing any impurities from the organic solvent. "Impurities" typically comprise chlorinated organics and hydrochloric acid. One method of removing these impurities is by distilling the organic solvent, with low boiling impurities being removed overhead and high boiling impurities being removed from the bottom of the distillation device. After distilling, impurities such as hydrochloric acid may further be removed by passing the distilled organic solvent through an ion exchange resin.

Once the HOCl has been stripped from the solvent it is absorbed in water as in the first method described for making the HOCl. As in the first HOCl method, after an initial run-through of the method for producing epoxides of this invention, the water of Step (e) in this HOCl method (Step (a) of the epoxide method), is comprised of water recycled from Step (b) of the epoxide method (discussed infra). Additional, non-recycled, water may also be supplemented to this recycled water.

Finally, a more preferred method for forming the low chlorides aqueous HOCl solution comprises, first, contacting solid sodium carbonate ($Na_2CO_3$) with a chlorine gas containing composition mixed with water vapor to form an off-gas composition comprising dichlorine monoxide ($Cl_2O$) vapor and carbon dioxide vapor. Solid sodium chloride is produced as a byproduct of this reaction. A second step is then to absorb the dichlorine monoxide into water. Similar approaches for forming the HOCl solution are described in U.S. Pat. Nos. 4,190,638, 2,155,281, 2,157,524, 2,157,525, and 3,914,397, and the relevant portions of these patents are incorporated herein by reference. Preferably, the solid sodium carbonate is anhydrous. When anhydrous sodium carbonate is used for contacting with the water vapor and chlorine gas containing mixture, HOCl is formed as an off-gas along with the dichlorine monoxide and carbon dioxide. More preferably, a humidified gas mixture of chlorine and nitrogen is passed through a bed of anhydrous sodium carbonate and the off-gasses are absorbed into aqueous distillation bottoms until a desired concentration of HOCl is reached. The nitrogen serves as a carrier and to dilute the dichlorine monoxide to prevent having an explosive atmosphere. As in the other HOCl methods, after an initial run-through of the method for producing epoxides of this invention, the water used for the absorption is comprised of water recycled from Step (b) of the epoxide method (discussed infra). Additional, non-recycled, water may also be supplemented to this recycled water.

When forming low chlorides aqueous HOCl solution in this manner, it is typically beneficial to supply the chlorine gas containing composition in excess to the solid sodium carbonate. When this is done, unreacted chlorine gas containing composition may be recycled back for further contact with the solid sodium carbonate. The solid sodium chloride byproduct may also be recycled by dissolving it in water to form brine, and then forwarding it to a chlor-alkali electrochemical cell, as described above.

Once the low chlorides aqueous HOCl solution is formed, the method of this invention for producing epoxides comprises contacting the low chlorides aqueous HOCl solution with at least one unsaturated organic compound to form an aqueous organic product comprising at least olefin chlorohydrin ("chlorohydrin forming step"). The "unsaturated organic compound" may contain from 2 to about 10 carbon atoms, preferably 2 to 8 carbons, and more preferably 2 to 6 carbons. The organic compound is selected from a group consisting of substituted and unsubstituted olefins and may be linear, branched, or cyclic, preferably linear. Suitable olefins include amylenes, allene, butadiene, isoprene, allyl alcohol, cinnamyl alcohol, acrolein, mesityl oxide, allyl acetate, allyl ethers, vinyl chloride, allyl bromide, methallyl chloride, propylene, butylene, ethylene, styrene and allyl chloride and their homologues and analogs. Propylene, butylene, ethylene, styrene and allyl chloride are the preferred olefins; with propylene, butylene, and allyl chloride more preferred and propylene most preferred. The olefin is preferably unsubstituted, but may also be inertly substituted. By "inertly" it is meant that the olefin is substituted with any group which does not undesirable interfere with formation of the chlorohydrin or the epoxide. Inert substituents include chlorine, fluorine, phenyl, and the like. A relevant description of a chlorohydrin forming step is disclosed in copending U.S. patent application Ser. No. 08/156,507 (incorporated herein by reference).

For optimum results, the organic compound is typically added in an amount sufficient to provide a molar ratio of organic compound to low chlorides HOCl of greater than 0.8. To insure complete reaction of the HOCl, the amount of organic compound is advantageously provided in an amount of at least about stoichiometric. Preferably from about 0 to about 25 mole percent of excess organic compound is provided, and more preferably from about 1 to about 10 mole percent excess organic compound is fed to the reactor. Unreacted organic compound may then be recycled back to contact with the HOCl. A skilled artisan is fully capable of employing various known methods of recycling unreacted organic compounds when the compounds are supplied in excess of that needed for the reaction. The incoming feed of low chlorides aqueous HOCl is typically provided in a concentration of from about 1.0 to about 10 wt-%, preferably from about 3 to about 7 wt-%, more preferably from about 4 to about 5 wt-%, based on HOCl in water. This provides a good balance between water requirements and inhibition of by-product formation.

The organic compound may be contacted with the HOCl solution by any method sufficient to form the chlorohydrin. This is typically accomplished by introducing the organic compound and the HOCl solution into a reactor in a manner so as to allow maximum uniformity of all of the reactor's contents. Preferably, the contact of the HOCl solution and the organic compound occurs in either a continuous or semi-continuous reactor. In a continuous reactor, such as a continuous tubular reactor, reactants are introduced and products withdrawn simultaneously. In contrast, an example of a semi-continuous reactor would be a reactor having a specific amount of organic compound already placed in the reactor, then having a continuous feed of the HOCl solution fed to the reactor, producing chlorohydrin products which accumulate in the reactor. It is more preferred that the contact occur in the presence of mixing in a continuous reactor such as a plug flow reactor or a backmix reactor. A plug flow reactor is one in which reactants are introduced at one end and products withdrawn at the other end with little backmixing along the reactor, for example, a continuous tubular reactor. A backmix reactor is defined as a reactor in which reaction products are intimately mixed with feed materials, resulting in uniform product and reactant concentrations throughout the reaction vessel. An example of a continuous reactor of this type is a continuous-flow stirred tank reactor (CSTR).

Conditions of temperature, pressure and reaction time are not critical. Any conditions under which the HOCl and the organic compound react are suitably used. The HOCl solution is advantageously fed to the reactor at a temperature of about 30°–60° C., preferably about 40° C. Conveniently, the temperature of the HOCl/organic compound reaction is at least about 40° C. because lower temperatures require refrigeration or other cooling. More preferably, the reaction temperature is at least about 60° C. Preferably, the temperature is less than about 100° C., more preferably less than about 90° C. (to avoid vaporization of the water and organic compounds in the reactor), and most preferably less than about 80° C. (to avoid undesirable increases in by-product formation).

In the most preferred embodiment, when a CSTR is used, it operates isothermally, whereas a plug flow type reactor commonly operates adiabatically. The heat of reaction is, therefore, advantageously removed from a CSTR such as by a recycle heat exchanger and/or a reactor jacket. To minimize the external heating or cooling on the reactor, the heat of reaction is preferably matched with raw material feed temperatures such that the heat of reaction raises the feed temperatures to the desired reaction temperature. Matching the temperatures is within the skill in the art. For example a one molar HOCl feed concentration (about 5 weight percent HOCl) reacted with propylene adiabatically raises the temperature about 55° C. Therefore, if a reaction temperature of about 90° C. is desired, the feed temperature is advantageously about 35° C. A lesser spread between feed temperature and reaction temperature requires cooling, while a greater spread in temperatures requires heating. The temperature control is achieved by any means within the skill of the art, such as a jacketed reaction vessel, submersible coils in the reactor, or a heat exchanger in an external recycle line.

Conveniently, the pressure is at least about atmospheric (about 101 kPa), preferably at least about 2 atmospheres (202.6 kPa) gauge, more preferably at least about 4 atmospheres (405.6 kPa) gauge. The higher pressures enhance the mass transfer of the organic compound with the HOCl solution, increasing the overall reaction rate. Conveniently, the pressure is less than about 150 psig (1037 kPa) gauge, more preferably less than about 100 psig (691 kPa) gauge, because the lower pressure requirements reduce the fabrication costs of the reactor.

The reaction time for the chlorohydrin forming step varies depending upon such factors as reactants used, reaction temperature, desired conversion level, agitation, excess organic compound, reactor pressure (when the organic compound is a gas), chlorides level in the HOCl feed, and HOCl feed concentration. One skilled in the art is capable of determining the sufficient time required for reaction of the HOCl with the organic compound. For example, when propylene is used as the organic compound in a CSTR, and under the above described most preferred conditions, reaction time is preferably at least about 5 minutes and more preferably at least about 10 minutes. Conveniently, the reaction time is less than about 30 minutes and more preferably less than about 15 minutes in order to minimize the size of the reactor vessel needed to produce a preselected amount of product.

Conversion of HOCl in the CSTR is advantageously at least about 90 mole percent and preferably greater than about 98 mole percent, such that the HOCl concentration in the reactor, diluted by water from reacted HOCl solution, does not exceed 0.2 wt-%, preferably less than 0.1 wt-%. Lower conversion levels result in higher yields of chlorinated ketones, such as monochloroacetone (MCA), from oxidation of the product chlorohydrin, such as propylene chlorohydrin (PCH). Advantageously, conversion is less than about 99.8 mole percent in the CSTR; higher conversions, though possible, require longer residence times, and thus, larger equipment to produce a preselected amount of product. Thus, for example, in a propylene (25 mole percent excess) reaction with 5 wt-% HOCl, containing 200 ppm chlorides, at 60° C. and 4 atmospheres (405.2 kPa) gauge pressure, using a gas-inducing impeller, 15 minutes are required for 99.5 mole percent conversion of the HOCl in the CSTR.

After the aqueous organic product comprising at least olefin chlorohydrin is formed in Step (b) ("chlorohydrin forming step"), water is recovered from the aqueous organic product. This water is then recycled back to use in forming the low chlorides aqueous HOCl solution (Step (a)). The water may be recovered by any means known in the art as long as the olefin chlorohydrin in the organic product is substantially isolated before continuing the method to Step (c). By "substantially isolated" it is meant that the olefin chlorohydrin is at least about 95% removed from the water, preferably at least about 99% removed from the water, and the water content of the olefin chlorohydrin is less than about 60 wt-%, preferably less than about 50 wt %.

One method for recovering the water is by distillation. For example, the aqueous organic product from Step (b) may be subjected to fractional distillation to separate a majority of the water from the organics, with the organics being recovered overhead as an azeotrope with water. A relevant description for azeotropic distillation of aqueous alkene halohydrin solutions is described in U.S. Pat. No. 2,188,254 (incorporated herein by reference). The distillation is conducted under such conditions that the olefin chlorohydrin is recovered in at least about 95%, preferably at least about 99% in the overheads distillate. Maximizing the recovery of the olefin chlorohydrin minimizes the organics remaining in the bottoms water for recycle. The operating conditions of temperature and pressure are a function of the olefin chlorohydrin to be stripped. Propylene chlorohydrin, for example, may be stripped at 95°–100° C. and atmospheric pressure. Conveniently, the chloride level in the feed to this distillation is low due to the use of low chlorides HOCl solutions in olefin chlorohydrin preparation; therefore, the chloride content of the bottoms water for recycle is also low. The overheads may then be used for epoxidation (Step (c)) and the water which is left behind as bottoms is recycled to make the low chlorides aqueous HOCl solution (Step (a)).

Another method for recovering the water from the aqueous organic product is by extracting the organic product from the water with an organic solvent. In general, such extraction is effected at an elevated temperature in that higher temperatures tend to favor the equilibrium concentration of the organic product in the organic solvent. Thus, for example, such extraction may be effected at temperatures in the order of from about 25° C. to about 90° C. Preferably, the organic solvent is a primary straight chain alcohol having from about 6 to about 12 carbon atoms. For example, octanol is a preferred organic solvent for performing this extraction.

Once the organic product is extracted it should be separated from the organic solvent. A preferable method for performing this separation is distillation. Another preferable method for performing this separation is to remove the organic solvent by a stripping operation utilizing live steam or olefin as a stripping agent. Once the organic solvent has been separated it may be recycled back for use in extracting the organic product again.

Once the water is recycled back to the low chlorides aqueous HOCl forming step (Step (a)), the organic product comprising at least the olefin chlorohydrin is contacted with an aqueous alkali metal hydroxide to form an aqueous salt solution product containing at least epoxide. This step (Step (c)) is also referred to as the saponification or epoxidation step. A relevant description of a saponification step is disclosed in copending U.S. patent application Ser. No. 08/156,507 (incorporated herein by reference). The major desired reaction is that of the olefin chlorohydrin with a base such as sodium hydroxide, potassium hydroxide, or calcium hydroxide, preferably an aqueous alkali metal hydroxide such as sodium hydroxide or potassium hydroxide, more preferably aqueous sodium hydroxide, and most preferably caustic from the chlor-alkali electrochemical cell (described above), to yield the corresponding epoxide. The amount and concentration of aqueous alkali metal hydroxide is suitably any which result in formation of the corresponding epoxide. Preferably, this amount is at least about 1.01 times stoichiometric based on chlorohydrin, more preferably at least about 1.05 times stoichiometric. Excess aqueous alkali metal hydroxide is beneficial to increase pH in order to reduce the rate of hydrolysis of the epoxides to glycols as compared to the rate under acidic conditions. A particularly preferable amount of aqueous alkali metal hydroxide is that sufficient to provide a pH of at least about 11. A concentration of at least about 1 wt-% aqueous alkali metal hydroxide is preferred, more preferably at least about 4 wt-%.

Conditions of temperature, pressure and reaction time are not critical, and any under which the chlorohydrin and aqueous alkali metal hydroxide react to produce at least an epoxide are suitable. The rate of a chlorohydrin's reaction with the base, such as for example propylene chlorohydrin with caustic in an amount of 8 wt-% sodium hydroxide, is very fast, requiring about 1 second to go to 99.5 mole percent completion under conditions of 90° C. The temperature and pressure are preferably controlled to prevent chlorohydrin vaporization. For example, for propylene chlorohydrin, this would be less than about 95° C. at one atmosphere pressure (101.3 kPa). Conveniently, the temperature is at least about 70° C. and more preferably at least about 85° C. At this more preferred temperature, the rate of reaction between aqueous alkali metal hydroxide and chlorohydrin is maximized and, since epoxide hydrolysis to glycols is a function of epoxide concentration in solution, allows vaporization of the product epoxide as soon as it is formed, minimizing the hydrolysis reaction of epoxide to glycol.

After the epoxide is formed in the saponification step (Step (c)), the next step is to isolate the epoxide from the aqueous salt solution. This is achieved by any process which results in separation of the epoxide. Such processes are within the skill in the art such as distillation or steam stripping. For example, both copending U.S. patent application Ser. No. 08/156,507 and U.S. Pat. No. 3,886,187 describe such processes and are each incorporated herein by reference. As applied to this invention, the aqueous salt solution product containing at least epoxide from Step (c) may be fed to the top of a stripping column. An initial separation of the vapor (containing epoxide, water vapor, and some by-product organic compounds) and the liquid brine occurs in the head space of the column. The liquid brine then flows downward through either a tray or packed section where steam (about 1–2 kg steam per kg of epoxide formed from the saponification of a 5 wt-% epoxide solution) flowing upward contacts the liquid to strip the remaining dissolved epoxide from solution. For propylene oxide, the conditions of this separation are preferably 90°–120° C. and 0.6 to 2.0 atmospheres absolute pressure (60.8 kPa to 202.6 kPa). The vapor containing the epoxide, water vapor (steam), and by-product organic compounds is taken overhead, where a partial condensation is optionally carried out to reflux part of the water to the stripping column. Little or no epoxide is refluxed, minimizing glycol formation. The remainder of the vapor is then condensed before a final purification of the epoxide. Methods for purification of epoxide, particularly propylene oxide, are well established in the art and examples of such are described in U.S. Pat. Nos. 3,398,062, 3,282,966, and 4,243,492, each of which are incorporated herein by reference.

Once the epoxide has been separated from the aqueous salt solution, the aqueous salt solution (brine) may be recycled to a chlor-alkali electrochemical cell to produce products comprising chlorine and caustic, as described previously with respect to the low chlorides aqueous HOCl solution forming step (Step (a)). The chlorine and caustic may then be recycled back for use in the HOCl forming step (Step (a)), the saponification step (Step (c)), or a combination thereof. It is generally preferred, prior to recycling into the chlor-alkali electrochemical cell, to remove any impurities such as glycol from the brine. A method for removing these impurities may include, for example, chlorinolysis as is well known in the art. Chlorinolysis of the brine requires chlorine gas, which may be optionally supplied from acidification of impurities in Step (a). Representative methods for removing impurities from brine before passing through a chlor-alkali electrochemical cell are described in U.S. Pat. Nos. 4,126,526, 4,240,885, and 4,415,460 each of which are incorporated herein by reference. In addition, either before or after removing the impurities from the brine, but preferably after, the brine may be combined with the brine produced in the HOCl forming step (Step (a) of this invention). This combined brine stream may then be recycled through the chlor-alkali electrochemical cell and the products used in the method of this invention.

This invention will be further clarified by a consideration of the following examples, which are intended to be purely exemplary of the use of the invention. In these examples, all ratios, parts, and percentages are by weight unless otherwise designated.

EXAMPLES

EXAMPLE 1

HOCl GENERATION

Preparation of hypochlorous acid solution with low levels of chloride ion was accomplished with the following procedure. A mixture of 30 volume percent chlorine gas and 70 volume percent nitrogen was continuously sparged at a flowrate of 110 liters/hour through a gas washing bottle fitted with a fritted glass sparge tube filled with water and heated with a hot plate to 50° C. The gas passed to the bottom of an amber colored glass reactor vessel that had an inside diameter (ID) of 4 centimeters (cm) and was 90 cm tall. A medium frit glass support disc was located 4 cm from the bottom. The reactor was filled with 530 grams (g) of sodium carbonate. The gas entered the bottom of the reactor, passed through the support frit and then through the sodium carbonate. The gas exited the top of the reactor and went to an absorber filled with I liter of deionized water maintained at 10° C. The absorber was a 2 liter, amber, jacketed, roundbottom glass flask equipped with a recycle pump. The gas from the reactor was introduced to the absorber in a discharge line of the pump. Unabsorbed gases exited the top of the absorber flask where the excess chlorine was scrubbed with a 50 wt-% sodium hydroxide aqueous solution. Replacing the sodium carbonate in the reactor one time was necessary to achieve the desired hypochlorous acid concentration in the absorber due to depletion of sodium carbonate from the reaction with chlorine.

When the hypochlorous acid content in the absorber reached about 5 wt-%, the gas feed to the reactor was turned off and absorber contents were purged with nitrogen to remove dissolved chlorine. The absorber contained hypochlorous acid that was low in chloride ion and dissolved chlorine. The hypochlorous acid solution was transferred to a plastic storage bottle and stored in a dark place at 5° C. The above procedure was repeated until 4 liters of hypochlorous acid solution were collected. Analysis of the combined solutions showed 5.33 wt-% hypochlorous acid, 260 parts per million (ppm) chlorate ion, 300 ppm HCl, and a pH of 2.4.

EXAMPLE 2

HYPOCHLORINATION

The 5.33 wt. % hypochlorous acid solution from Example 1 was fed continuously at 30 g/min, along with propylene gas at 1050 ml/min, to a 13.7 meter (m) long reactor tube with a 6.35 millimeter (mm) ID. The reactor was shaped in a helical coil of polytetrafluoroethylene tubing with reactants entering the bottom and products exiting at the top of the coil. Propylene was used at 40 percent excess based on the stoichiometry with hypochlorous acid. The pressure was controlled at 108 kilo-Pascal (kPa). Eight thermocouples were evenly spaced along the reactor tube. Temperatures ranged from 40°–80° C. Electrical heating tapes were used to control the temperature profile. At the beginning of the reactor were 7.6 cm of in-line static mixers. Discharge from the reactor entered a cold jacketed degasser to vent any unreacted propylene. A liquid product was sampled and analyzed by gas chromatography for organic content. The selectivity of propylene to propylene chlorohydrin (PCH) was 91.4%.

EXAMPLE 3

PCH DISTILLATION

Propylene chlorohydrin and other organics from Example 2 were continuously distilled overhead as an azeotrope with water at atmospheric pressure. An Oldershaw glass distillation column with 36 sieve trays and a 25 mm ID was used. The feed entered the 11 th tray from the top of the column at 15 ml/min. A reboiler pot was used to provide boil up at 100° C. A 5:1 reflux ratio was used to produce a 50 wt % PCH concentration in an overheads product. The overheads and bottoms component analyses were done by gas chromatography. The bottoms contained water, 140 ppm by weight PCH, 430 ppm dichlorohydrin (1,3-dichloro-2-hydroxypropane and 2,3-dichloro-1-hydroxypropane), and 400 ppm total of other organics. The bottoms also contained 1140 ppm chloride ion and 114 ppm chlorate ion.

EXAMPLE 4

PCH EPOXIDATION/PO STRIPPING

Cell liquor (8% NaOH, 15% NaCl) from a chlor/alkali electrolytical cell and 50 wt-% PCH from the overheads of the PCH distillation column of Example 3 were continuously fed through an in-line static mixer to the top tray of a 137 cm tall, silvered 25 mm ID Oldershaw column which contained 36 sieve trays. The cell liquor (9.5 g/min) and PCH solution (4.6 g/min) were preheated to 85° C. prior to mixing together. Steam at 1.3 g/min was introduced below the bottom tray. The column overhead temperature was 81° C., the bottom temperature was 89° C., and the pressure was 72 kPa. The overhead vapor was condensed and analyzed by gas chromatography. The yield of propylene oxide from the starting PCH was 78 percent with 19.5 percent of the starting PCH unreacted. The bottoms aqueous brine contained 2.35 wt % NaOH, 17.2 wt % NaCl, 4050 ppm propylene glycol, and 350 ppm other organics.

EXAMPLE 5

CHLORINOLYSIS

The continuous chlorinolysis reaction unit consisted of a 60.5 cm long by 50 mm ID polytetrafluoroethylene-lined, vertically mounted pipe reactor with a vapor liquid disengagement system mounted on top of the reactor. The reactor was baffled using 39 horizontal, 3.2 mm thick polytetrafluoroethylene disks with a 20% baffle cut and a spacing of 16 mm. Cell liquor (8 wt-% NaOH, 15 wt-% NaCl) at 10 g/min was mixed in an in-line static mixer with the brine from Example 4 at 41.5 g/min and preheated to 112° C. Chlorine gas at 445 ml/min was added to the liquid feed and then introduced to the bottom of the reactor. Product exited the top of the reactor at 119° C. and 300 kPa. A Dewar flask was used to cool the reaction effluent using ice and water. Another Dewar flask was employed to condense any condensables coming from the vapor overheads using ice and water. Two 2.5-liter glass caustic scrubbers with fritted glass spargers were used to scrub any excess chlorine from the vapors. Analysis of the aqueous product and the condensed vapors showed 89.8 percent reduction in propylene glycol content and an overall reduction in organics of 58.7 percent. The product had 18.2 wt % NaCl, 1.2 wt % sodium carbonate, and 0.38 wt % sodium hypochlorite.

EXAMPLE 6

RECYCLE OF WATER

The procedure of Example I was repeated using the aqueous bottoms from the distillation column of Example 3 for the absorber water instead of fresh deionized water. Analysis of the hypochlorous acid solution showed 5.39 wt % hypochlorous acid, 230 ppm chlorate ion, 400 ppm chloride ion, a pH of 2.5, and 413 ppm total organics.

The procedure of Example 2 was repeated using this hypochlorous acid solution (hypochlorous acid content was adjusted to 5 percent by weight) to react with propylene. Selectivity of propylene to propylene chlorohydrin was 94.8 percent.

The procedure of Example 3 was repeated using this hypochlorination product. The bottoms water from the distillation column contained 550 ppm chloride ion, 200 ppm chlorate ion, 500 ppm dichlorohydrin, and 200 ppm other organics.

EXAMPLES 7–14

CONTINUED WATER RECYCLE

The procedure of Example 6 was repeated 8 times using the water from the distillation bottoms of the previous example for the absorber water in generating the hypochlorous acid solution. The results are shown in Table 1.

TABLE 1

| | | | | | | | |
|---|---|---|---|---|---|---|---|
| | Results of recycling water in the production of propylene chlorohydrin. | | | | | | |
| Example | Product | Cl- ppm | ClO3- ppm | pH | Dichlorohydrin ppm | Other Organics ppm | PCH Selectivity |
| 7 | HOCl | 510 | 290 | 2.8 | 570 | 200 | |
| | PCH | 210 | 250 | | | | 95.7 |
| | Water | 370 | 260 | | 1080 | 690 | |
| 8 | HOCl | 620 | 410 | 3.0 | 790 | 390 | |
| | PCH | 70 | 300 | | | | 95.0 |
| | Water | 150 | 350 | | 1350 | 580 | |
| 9 | HOCl | 660 | 365 | 2.7 | 1220 | 390 | |
| | PCH | 110 | 320 | | | | 95.5 |
| | Water | 130 | 360 | | 2180 | 1145 | |
| 10 | HOCl | 950 | 380 | 2.6 | 1930 | 850 | |
| | PCH | 1090 | 310 | | | | 90.1 |
| | Water | 1360 | 350 | | 1770 | 300 | |
| 11 | HOCl | 700 | 360 | 2.7 | 920 | 135 | |
| | PCH | 350 | 300 | | | | 94.0 |
| | Water | 710 | 310 | | 1750 | 310 | |
| 12 | HOCl | 960 | 490 | 2.7 | 1060 | 190 | |
| | PCH | 150 | 310 | | | | 94.9 |
| | Water | 370 | 320 | | 1400 | 220 | |
| 13 | HOCl | 850 | 350 | 2.7 | 1080 | 180 | |
| | PCH | 270 | 310 | | | | 95.0 |
| | Water | 400 | 360 | | 1350 | 250 | |
| 14 | HOCl | 1000 | 380 | 2.6 | 1120 | 90 | |
| | PCH | 270 | 320 | | | | 94.2 |
| | Water | 550 | 320 | | 1440 | 325 | |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A method for producing epoxides comprising the steps:
   (a) forming a low chlorides aqueous hypochlorous acid solution;
   (b) contacting the low chlorides aqueous hypochlorous acid solution with at least one unsaturated organic compound to form an aqueous organic product comprising at least olefin chlorohydrin, wherein the unsaturated organic compound contains from 2 to about 10 carbon atoms and is selected from the group consisting of substituted and unsubstituted olefins and cyclic olefins, the substituted olefins having substituents selected from the group consisting of an alkyl radical, a phenyl radical, and an alkylphenyl radical, each radical being independently either unsubstituted or substituted;
   (c) contacting at least the olefin chlorohydrin with an aqueous alkali metal hydroxide to form an aqueous salt solution product containing at least epoxide; and
   (d) isolating the epoxide from the aqueous salt solution;
   wherein water is recovered from the product of at least Step (b) and recycled into Step (a) for use in forming the low chlorides aqueous hypochlorous acid solution.

2. The method of claim 1 wherein the water is recovered from the product of Step (b) by distilling the organic product comprising at least olefin chlorohydrin from the water.

3. The method of claim I wherein the water is recovered from the product of Step (b) by extracting the organic product from the water with an organic solvent.

4. The method of claim 3 wherein the organic solvent is a primary straight chain alcohol having from about 6 to about 12 carbon atoms.

5. The method of claim 4 wherein the primary straight chain alcohol is octanol.

6. The method of claim 3 wherein the extracted organic product is separated from the organic solvent.

7. The method of claim 6 wherein the organic solvent is recycled for use in extracting the organic product.

8. The method of claim 1 wherein the unsaturated organic compound of Step (b) is selected from ethylene, propylene, butylene, 3-chloropropene, allyl alcohol, allyl chloride, 1-hexene, cyclohexene, styrene, and mixtures thereof.

9. The method of claim 1 wherein the unsaturated organic compound of Step (b) is selected from the group consisting of propylene, butylene, and allyl chloride.

10. The method of claim 1 wherein the contacting of Step (b) is done in a continuous process using a continuous stirred tank reactor with backmix stirring sufficient to maintain the HOCl concentration in the reactor of 0.2 weight percent or less.

11. The method of claim 1 wherein the aqueous alkali metal hydroxide of Step (c) is caustic from a chlor-alkali electrochemical cell.

12. The method of claim 1 wherein at least one of the alkali metals in the aqueous alkali metal hydroxide is selected from the group consisting of sodium and potassium.

13. The method of claim 12 wherein the aqueous alkali metal hydroxide comprises aqueous sodium hydroxide.

14. The method of claim 1 wherein the epoxide of Step (d) is isolated from the aqueous salt solution by distillation.

15. The method of claim 1 further comprising recycling the aqueous salt solution from Step (d) to a chlor-alkali electrochemical cell to form products comprising chlorine and caustic.

16. The method of claim 15 wherein the chlorine and caustic are recycled back for use in any of Steps (a), (c), or a combination thereof.

17. The method of claim 15 wherein, before recycling to the chlor-alkali electrochemical cell, the aqueous salt solution from Step (d) is combined with an aqueous salt solution produced from forming low chlorides aqueous hypochlorous acid in Step (a).

18. The method of claim 1 wherein the low chlorides aqueous hypochlorous acid solution of Step (a) is formed by a method comprising the steps:
   (a) contacting an aqueous alkali metal hydroxide solution with chlorine to produce an aqueous alkali metal hypochlorite solution;
   (b) contacting droplets of the aqueous alkali metal hypochlorite solution with chlorine gas to produce aqueous hypochlorous acid;
   (c) vaporizing at least about 30 weight percent of the aqueous hypochlorous acid to produce a vapor phase and a liquid phase, the vapor phase comprising chlorine, water vapor, hypochlorous acid, and dichlorine monoxide, the liquid phase comprising hypochlorous acid in an aqueous salt solution;
   (d) distilling the liquid phase using a vapor stripping stream containing at least about 20 mole percent chlorine to strip vapor phase hypochlorous acid and dichlorine monoxide from the aqueous salt solution; and
   (e) absorbing the vapor phase hypochlorous acid and dichlorine monoxide from both Steps (c) and (d) into water.

19. The method of claim 18 wherein the alkali metal hydroxide is sodium hydroxide and the alkali metal hypochlorite is sodium hypochlorite.

20. The method of claim 18 wherein the alkali metal hydroxide is caustic from a chlor-alkali electrochemical cell.

21. The method of claim 18 further comprising collecting gases after Step (e) and recycling the gases to Step (d) for use in the vapor stripping stream.

22. The method of claim 1 wherein the low chlorides aqueous hypochlorous acid solution of Step (a) is formed by a method comprising:
   (a) contacting solid sodium carbonate with a chlorine gas containing composition to form a composition comprising dichlorine monoxide vapor and carbon dioxide vapor; and
   (b) absorbing the dichlorine monoxide into water.

23. The method of claim 22 wherein the chlorine gas containing composition further comprises water vapor.

24. The method of claim 22 wherein any unreacted chlorine gas containing composition from Step (a) is recycled back to Step (a) for contact with the solid sodium carbonate.

25. The method of claim 22 wherein solid sodium chloride is formed as a byproduct in Step (a), is dissolved in water, and is recycled to a chlor-alkali electrochemical cell to form products comprising chlorine and caustic.

26. The method of claim 1 wherein the low chlorides aqueous hypochlorous acid solution of Step (a) is formed by a method comprising:
   (a) contacting an aqueous alkali metal hydroxide solution with chlorine to produce an aqueous alkali metal hypochlorite solution;
   (b) contacting droplets of the aqueous alkali metal hypochlorite solution with chlorine gas to produce hypochlorous acid in an aqueous salt solution;

(c) extracting the hypochlorous acid from the aqueous salt solution using an organic solvent;

(d) stripping the hypochlorous acid from the organic solvent using a non-reactive gas; and (e) absorbing the stripped hypochlorous acid into water.

27. The method of claim 26 wherein the organic solvent is a ketone.

28. The method of claim 27 wherein the ketone is methyl isobutylketone.

29. The method of claim 26, Step (c), further comprising:

(a) distilling the extracted aqueous salt solution using a vapor stripping stream to strip hypochlorous acid and organic solvent from the extracted aqueous salt solution; and (b) combining the stripped hypochlorous acid and organic solvent with the extracted hypochlorous acid and organic solvent.

30. The method of claim 26 further comprising a step of recycling the aqueous salt solution to a chlor-alkali electrochemical cell to form chlorine and caustic.

31. The method of claim 26 wherein the non-reactive gas is selected from nitrogen or water vapor.

32. The method of claim 26 further comprising recycling the organic solvent from Step (d) back to Step (c).

* * * * *